United States Patent
Lee et al.

(10) Patent No.: US 10,357,182 B2
(45) Date of Patent: Jul. 23, 2019

(54) METHOD AND DEVICE FOR CONTROLLING MRI NOISE

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Gun-woo Lee, Suwon-si (KR); Nokhaeng Lee, Daejeon (KR); Sang-chul Ko, Seoul (KR); Youngjin Park, Daejeon (KR)

(73) Assignees: SAMSUNG ELECRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 171 days.

(21) Appl. No.: 15/514,621

(22) PCT Filed: Sep. 22, 2015

(86) PCT No.: PCT/KR2015/009931
§ 371 (c)(1),
(2) Date: Mar. 27, 2017

(87) PCT Pub. No.: WO2016/047997
PCT Pub. Date: Mar. 31, 2016

(65) Prior Publication Data
US 2017/0209069 A1    Jul. 27, 2017

Related U.S. Application Data

(60) Provisional application No. 62/055,157, filed on Sep. 25, 2014.

(51) Int. Cl.
*A61B 5/055* (2006.01)
*G01R 33/385* (2006.01)
(Continued)

(52) U.S. Cl.
CPC ............ *A61B 5/055* (2013.01); *A61B 5/7203* (2013.01); *G01R 33/385* (2013.01); *G01R 33/543* (2013.01)

(58) Field of Classification Search
CPC .......................... G01R 33/385; G01R 33/543
See application file for complete search history.

(56) References Cited

U.S. PATENT DOCUMENTS

| 5,427,102 A | 6/1995 | Shimode et al. |
| 5,481,192 A | 1/1996 | Mehlkopf et al. |

(Continued)

FOREIGN PATENT DOCUMENTS

| JP | 6-261888 A | 9/1994 |
| JP | 2007-268028 A | 10/2007 |

(Continued)

OTHER PUBLICATIONS

Search Reporting dated Jan. 13, 2016, issued by the International Searching Authority in counterpart International Patent Application No. PCT/KR2015/009931 (PCT/ISA/210).

(Continued)

*Primary Examiner* — Gregory H Curran
(74) *Attorney, Agent, or Firm* — Sughrue Mion, PLLC

(57) ABSTRACT

A device according to one disclosed embodiment comprises: a control part which determines at least one target frequency of an MRI noise signal generated in an MRI device and generates a control signal for the determined target frequency; and an output part which outputs the control signal, wherein the target frequency is the frequency of the MRI noise signal to be controlled and the control signal is a signal (Continued)

in which at least one of the size and the phase of the MRI noise signal is changed.

17 Claims, 7 Drawing Sheets

(51) Int. Cl.
*G01R 33/54* (2006.01)
*A61B 5/00* (2006.01)

(56) References Cited

U.S. PATENT DOCUMENTS

| | | | |
|---|---|---|---|
| 6,463,316 | B1 | 10/2002 | Brungart |
| 9,207,295 | B2 | 12/2015 | Yang |
| 2003/0187527 | A1* | 10/2003 | Delchar ............... G10K 11/178 700/94 |
| 2005/0053244 | A1* | 3/2005 | Onishi ............. G10K 11/17883 381/71.11 |
| 2009/0046868 | A1* | 2/2009 | Engle ................... H04R 1/1041 381/74 |
| 2013/0154647 | A1* | 6/2013 | Yang ..................... G01R 33/283 324/318 |

FOREIGN PATENT DOCUMENTS

| | | |
|---|---|---|
| JP | 2009-291484 A | 12/2009 |
| KR | 10-2013-0067433 A | 6/2013 |

OTHER PUBLICATIONS

Written Opinion dated Jan. 13, 2016, issued by the International Searching Authority in counterpart International Patent Application No. PCT/KR2015/009931 (PCT/ISA/237).

* cited by examiner

METHOD AND DEVICE FOR CONTROLLING MRI NOISE

TECHNICAL FIELD

The present invention relates to a method and apparatus for controlling magnetic resonance imaging (MRI) noise, and more particularly, to a method and apparatus for controlling MRI noise at individual frequencies by using information about MRI noise characteristics.

BACKGROUND ART

Along with increasing interest in healthcare, the development of cutting-edge medical equipment is also being accelerated. Magnetic resonance imaging (MRI) may provide doctors or patients with a lot of information by accurately showing detailed images of an internal area of the human body. With its technological advancements, MRI has been developed to obtain a more accurate image in a shorter time. However, as the strength of a magnetic field used to obtain a more accurate image increases, the level of noise generated during an MRI scan increases.

A gradient magnetic field is a main cause of MRI noise. A sudden change in current within a gradient coil under a static magnetic field produces a strong Lorentz force on the gradient coil. Noise is generated when the force causes motion and vibrations in the gradient coil.

Noise generated by an MRI system may cause discomfort to a patient, increase a patient's feeling of anxiety, and hamper verbal communication between a patient and a medical expert. Furthermore, due to exposure to noise, a patient may experience transient hearing loss, and in severe cases, permanent hearing impairment.

DETAILED DESCRIPTION OF THE INVENTION

Advantageous Effects of the Invention

Provided are a method and apparatus for controlling magnetic resonance imaging (MRI) noise, whereby a control signal necessary for performing active noise control may be generated by analyzing period information of the MRI noise and the MRI noise may be efficiently controlled using the generated control signal.

In addition, technical problems and advantageous effects of the present invention are not limited to the above-described features, and other technical problems not described herein will become readily apparent to those of ordinary skill in the art from the following detailed description.

BEST MODE

Figure 1:
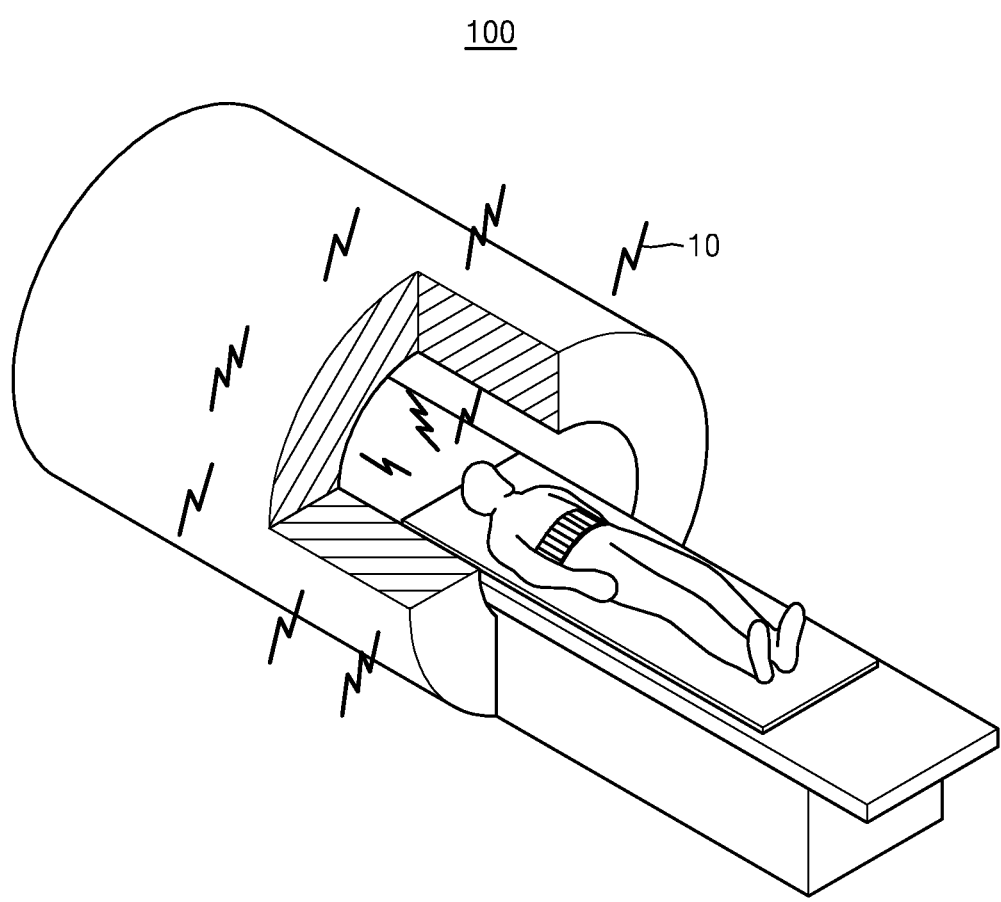
FIG. 1 illustrates a magnetic resonance imaging (MRI) system according to an embodiment.

An apparatus according to an embodiment disclosed herein includes a controller configured to determine one or more target frequencies of a magnetic resonance imaging (MRI) noise signal generated in an MRI system and generate a control signal for each of the determined one or more target frequencies, and a speaker configured to output the control signal. The target frequency is a desired frequency of the MRI noise signal to be controlled, and the control signal is a signal obtained by changing at least one of an amplitude and a phase of the MRI noise signal.

The apparatus may further include an acquisition unit configured to acquire the MRI noise signal at a desired position where the MRI noise signal is to be controlled.

The controller is further configured to determine a fundamental frequency of the MRI noise signal, determine one or more harmonic frequencies of the determined fundamental frequency, and determine the one or more target frequencies among the one or more harmonic frequencies.

The one or more target frequencies may be a predetermined number of harmonic frequencies that are selected from among the determined one or more harmonic frequencies based on energy information at each frequency.

The one or more target frequencies may be a predetermined number of harmonic frequencies that are selected from among the determined one or more harmonic frequencies based on coherence between the speaker and the acquisition unit.

The fundamental frequency may be determined by determining a period of the MRI noise signal based on information about an MRI sequence used to drive a gradient coil in the MRI system, and the fundamental frequency may be determined based on the determined period.

The fundamental frequency may be determined by determining a period of the MRI noise signal by analyzing the MRI noise signal acquired by the acquisition unit, and the fundamental frequency may be determined based on the determined period.

The control signal may reach a position of the acquisition unit through a transfer function and cancel out the MRI noise signal. The controller is further configured to generate a reference signal that becomes the basis of the control signal for each of the one or more target frequencies.

The reference signal generated for each of the one or more target frequencies may include a cosine wave and a sine wave that have the target frequency as a fundamental frequency.

The controller is further configured to perform a Fourier series expansion on the MRI noise signal, which has been acquired by the acquisition unit during a predetermined time period, for each of the one or more target frequencies to thereby determine an amplitude and a phase of the MRI noise signal, and apply the determined amplitude and phase to the reference signal generated for each of the one or more target frequencies to thereby generate the control signal.

A method according to an embodiment disclosed herein includes: determining one or more target frequencies of an MRI noise signal generated in an MRI system; generating a control signal for each of the determined one or more target frequencies; and outputting the generated control signal, wherein the target frequency is a desired frequency of the MRI noise signal to be controlled, and the control signal is a signal obtained by changing at least one of an amplitude and a phase of the MRI noise signal.

The method may further include acquiring the MRI noise signal at a desired position where the MRI noise signal is to be controlled.

The determining of the one or more target frequencies may include determining a fundamental frequency of the MRI noise signal, determining one or more harmonic frequencies of the determined fundamental frequency, and determining the one or more target frequencies among the one or more harmonic frequencies.

The control signal may reach a position of the acquisition unit through a transfer function to cancel out the MRI noise signal, and the generating of the control signal for each of the determined one or more target frequencies may include: generating a reference signal that becomes a basis of the control signal for each of the one or more target frequencies; performing a Fourier series expansion on the MRI noise signal, which has been acquired by the acquisition unit during a predetermined time period, for each of the one or more target frequencies to thereby determine an amplitude and a phase of the MRI noise signal; and applying the determined amplitude and phase to the reference signal generated for each of the one or more target frequencies to thereby generate the control signal.

A non-transitory computer-readable recording medium having recorded thereon a program for executing the method according to the embodiment on a computer may be provided.

MODE OF THE INVENTION

Hereinafter, embodiments will be described in more detail with reference to the accompanying drawings. The embodiments described in the present specification and configurations illustrated in the drawings are merely embodiments but do not represent all of the technical spirit of the present invention. Thus, the present invention should be construed as including all the changes, equivalents, and substitutions included in the spirit and scope of the present invention at the time of filing this application.

FIG. 1 illustrates a magnetic resonance imaging (MRI) system 100 according to an embodiment.

The MRI system 100 according to the embodiment is an apparatus for acquiring a sectional image of a part of an object by expressing, via a contrast comparison, strength of a magnetic resonance (MR) signal with respect to an RF signal generated in a magnetic field having a specific strength. For example, the MRI system 100 may instantaneously emit an RF signal that resonates only a specific atomic nucleus (for example, a nucleus of a hydrogen atom, etc.) in a strong magnetic field and then stop the emission. Due to the instantaneous emission of the RF signal, an MR signal is emitted from the specific atomic nucleus, and thus, the MRI system may receive the MR signal to obtain an MR image. The MR signal denotes an RF signal emitted from the object. An amplitude of the MR signal may be determined according to at least one of a density of a predetermined atom (for example, hydrogen, etc.) in the object, a T1 relaxation time, a T2 relaxation time, and blood flow, but embodiments are not limited thereto.

A sudden change in current within a gradient coil in the presence of a static magnetic field produces a strong Lorentz force on the gradient coil. Noise is generated in the MRI system 100 according to the embodiment when the force causes motion and vibrations in the gradient coil.

Thus, pulse sequences, such as fast gradient echo (FGE), echo planar imaging (EPI), and fast spin echo (FSE) sequences requiring extremely fast switching of gradient magnetic fields and high gradient magnetic fields, may generate high levels of noise. Consequently, a level of noise generated during an MRI scan may be dependent on the type of a pulse sequence used for imaging.

The MRI system 100 may decrease an MRI noise level by reducing instantaneous changes in current flowing through a gradient coil and an intensity of current. For example, the MRI system 100 may lower a noise level by reducing a slew rate and an amplitude of magnetic field applied to the gradient coil. A slew rate is defined as a rate of change of a gradient magnetic field (T/m/s) induced by current applied to a gradient coil, or a rising time taken for a gradient magnetic field to reach its maximum amplitude.

However, MRI noise may arise from various sources. Thus, it is difficult to calculate a noise level in a specific protocol by taking all factors into consideration.

For example, an MRI noise level tends to increase when a section thickness, a field of view (FOV), repetition time (TR), or echo time (TE) decreases.

A level of noise generated in the MRI system 100 may vary according to hardware of the MRI system 100 and the surrounding environment. Furthermore, a noise level may have a spatial dependence. For example, a noise level difference of about 10 dB may occur according to a position of a patient within a bore of the MRI system 100. The presence/absence and size of the patient may also affect the noise level.

Figure 2:
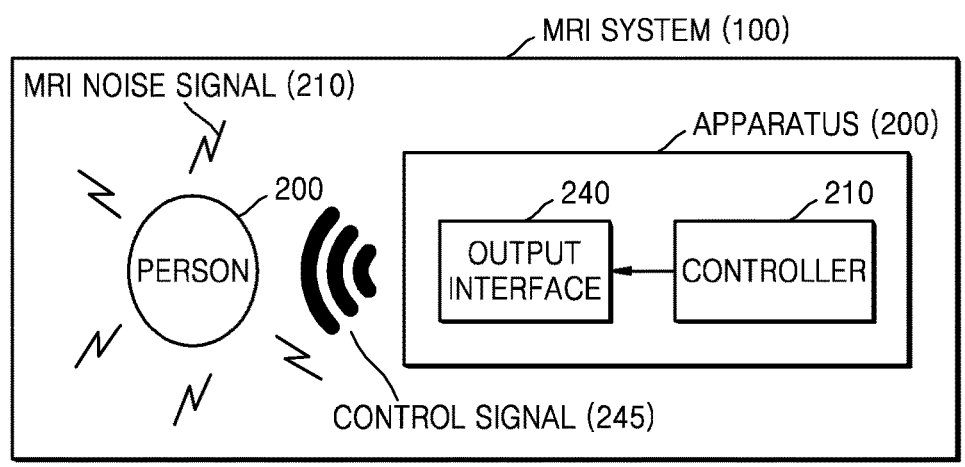
FIG. 2 is a diagram showing control of MRI noise by an apparatus according to an embodiment.

FIG. 2 is a diagram showing control of MRI noise by an apparatus 200 according to an embodiment.

Although FIG. 2 shows that the apparatus 200 is located within an MRI system 100, the apparatus 200 or at least one of an output interface 240 and a controller 210 of the apparatus 200 may be provided outside the MRI system 100.

As described with reference to FIG. 1, an MRI noise signal 210 represents noise generated in the MRI system 100.

The controller 210 may determine one or more target frequencies of the MRI noise signal 210 generated in the MRI system 100 and generate a control signal for each of the determined one or more target frequencies.

The output interface 240 may output a control signal 245. The output interface 240 may include a speaker for outputting the control signal 245. The control signal 245 may be a signal obtained by at least one of an amplitude and a phase of the MRI noise signal 210. The control signal 245 may be a signal obtained by adding together all control signals respectively generated by the controller 210 at the one or more target frequencies. Hereinafter, a 'control signal' may mean a control signal generated at each target frequency or the sum of all control signals respectively generated at one or more target frequencies. The control signal 245 output from the output interface 240 may cancel out and control the MRI noise signal 210, so that a person 220 can hear a reduced level of the MRI noise signal 210.

The apparatus 200 according to the embodiment may reduce noise that is heard by the person 220 placed within the MRI system 100 by cancelling out the original MRI noise signal 210 and the control signal 245 output from the output interface 240 at a desired position where the MRI noise signal 210 is to be controlled. The apparatus 200 may generate a control signal that is opposite to the MRI noise signal 210 at each frequency based on frequency information of the MRI noise signal 210.

Figure 3:
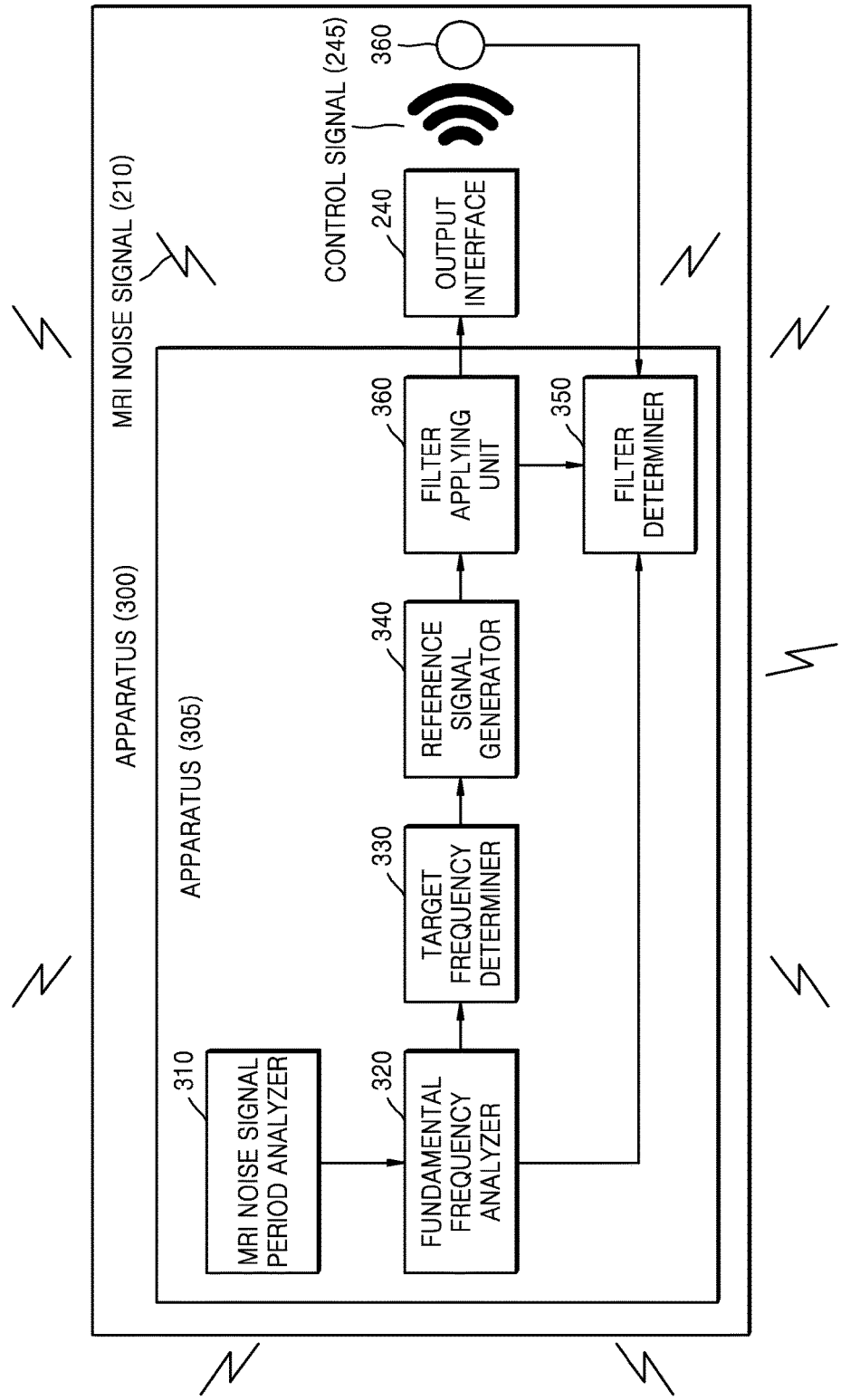
FIG. 3 is a diagram of a structure of an apparatus according to a detailed embodiment.

FIG. 3 is a diagram of a structure of an apparatus 300 according to a detailed embodiment.

The apparatus 300 of FIG. 3 is a detailed embodiment of the apparatus 200 of FIG. 2. Thus, the apparatus 200 and the controller 210 may respectively be implemented as the apparatus 300 and a controller 305, and the following descriptions of the apparatus 300 and the controller 305 may be applied to the apparatus 200 and the controller 210.

The apparatus 300 according to the embodiment may analyze primary information of an MRI sequence and MRI noise acquired via an acquisition unit 360 to thereby obtain period information of the MRI noise, generate a control signal 245 necessary for performing active noise control at each frequency based on the obtained period information, and reduce an MRI noise signal 210 by using the generated control signal 245.

The apparatus 300 according to the embodiment may include the controller 305, an output interface 240, and an acquisition unit 360.

The controller 305 may be a processor, an application specific integrated circuit (ASIC), an embedded processor, a microprocessor, a hardware control logic, a hardware finite state machine (FSM), a digital signal processor (DSP), or a combination thereof.

The controller 305 may determine one or more target frequencies of the MRI noise signal 210 generated in the MRI system 100 and generate the control signal 245 for each of the determined one or more target frequencies. The output interface 240 may output the control signal 245 generated by the controller 305. The control signal 245 output from the output interface 240 may reach a position of the acquisition unit 360 through a transfer function and cancel out the MRI noise signal 210 to control MRI noise at the position of the acquisition unit 360.

The acquisition unit 360 may acquire an MRI noise signal 210 at a desired position where the MRI noise signal 210 is to be controlled. Thus, the MRI noise signal 210 acquired by the acquisition unit 360 may be a noise signal obtained after the original MRI noise signal 210 is controlled by the control signal 245. The acquisition unit 360 may be implemented as any type of device configured to acquire the MRI noise signal 210, such as a microphone.

According to an embodiment, the controller 305 may include an MRI noise signal period analyzer 310, a fundamental frequency analyzer 320, a target frequency determiner 330, a reference signal generator 340, a filter applying unit 360, and a filter determiner 350.

The MRI noise signal period analyzer 310 may determine a period of the MRI noise signal 210 generated in the MRI system 100. According to an embodiment, the MRI noise signal period analyzer 310 may acquire MRI sequence period information from information about an MRI sequence used to drive a gradient coil in the MRI system 100. The MRI noise signal period analyzer 310 may determine a period of the MRI noise signal 210 based on the acquired MRI sequence period information.

According to an embodiment, when the MRI sequence period information is not acquired, the MRI noise signal period analyzer 310 may acquire information about a TR, which is a regular time interval at which an RF pulse of the MRI sequence is applied, and the number of slices. The MRI noise signal period analyzer 310 may acquire the information about MRI sequence before an MRI scan or after a gradient sequence is generated.

Alternatively, instead of acquiring the period information from the information about MRI sequence, the MRI noise signal period analyzer 310 may determine a period of the MRI noise signal 210 by analyzing the MRI noise signal 210 acquired by the acquisition unit 360.

The fundamental frequency analyzer 320 may determine a fundamental frequency of the MRI noise signal 210 based on the period of the MRI noise signal 210, which is determined by the MRI noise signal period analyzer 310. The fundamental frequency analyzer 320 may determine the fundamental frequency of the MRI noise signal 210 based on the MRI sequence period information acquired by the MRI noise signal period analyzer 310. The fundamental frequency analyzer 320 may determine a fundamental frequency of the MRI noise signal 210 by using Equation (1):

$$\text{fundamental frequency (Hz)} = 1/\text{period (sec)} \qquad \text{[Equation 1]}$$

where period (sec) represents MRI sequence period information acquired by the MRI noise signal period analyzer 310.

According to another embodiment, the fundamental frequency analyzer 320 may determine a fundamental frequency of the MRI noise signal 210 by using information about a TR and the number of slices in an MRI sequence.

$$\text{fundamental frequency (Hz)} = \text{slice number}/\text{TR value (msec)} \qquad \text{[Equation 2]}$$

According to another embodiment, the fundamental frequency analyzer 320 may determine a fundamental frequency of the MRI noise signal 210 by analyzing the MRI noise signal 210 acquired by the acquisition unit 360. The fundamental frequency analyzer 320 may store signals acquired during a specific time period T in a buffer and determine autocorrelation values for the stored signals. The fundamental frequency analyzer 320 may select a lag value Lag_Max (excluding a lag value of 0) having a maximum autocorrelation value among the determined autocorrelation values and determine a fundamental frequency of the MRI noise signal 210 according to Equation (3):

$$\text{fundamental frequency (Hz)} = \text{sampling frequency (Hz)}/\text{Lag\_Max} \qquad \text{[Equation 3]}$$

The target frequency determiner 330 may determine one or more target frequencies. A target frequency refers to a desired frequency of the MRI noise signal 210 to be controlled. Since the MRI noise signal 210 can be represented as a combination of harmonics of a fundamental frequency, one or more harmonic frequencies composing the MRI noise signal 210 may be determined using a fundamental frequency determined by the fundamental frequency analyzer 320. In other words, the target frequency determiner 330 may determine harmonic frequencies that are multiples of the fundamental frequency as being target frequencies.

According to an embodiment, the target frequency determiner 330 may determine one or more harmonic frequencies (f, 2*f, 3*f, . . . , fs/2 where f is a fundamental frequency), select, among the determined one or more harmonic frequencies, a predetermined number of frequencies sequentially from a frequency corresponding to highest energy by using energy information M with respect to each frequency, and determine the predetermined number of frequencies as being the target frequencies.

The target frequency determiner 330 may exclude, from target frequencies that are determined among the determined one or more harmonic frequencies, a frequency band in which the output interface 240 and the acquisition unit 360 have low coherence therebetween based on pre-analyzed system response characteristics. If the output interface 240 and the acquisition unit 360 have high coherence therebetween, this means that the acquisition unit 360 may successfully acquire a signal output from the output interface

Figure 4:
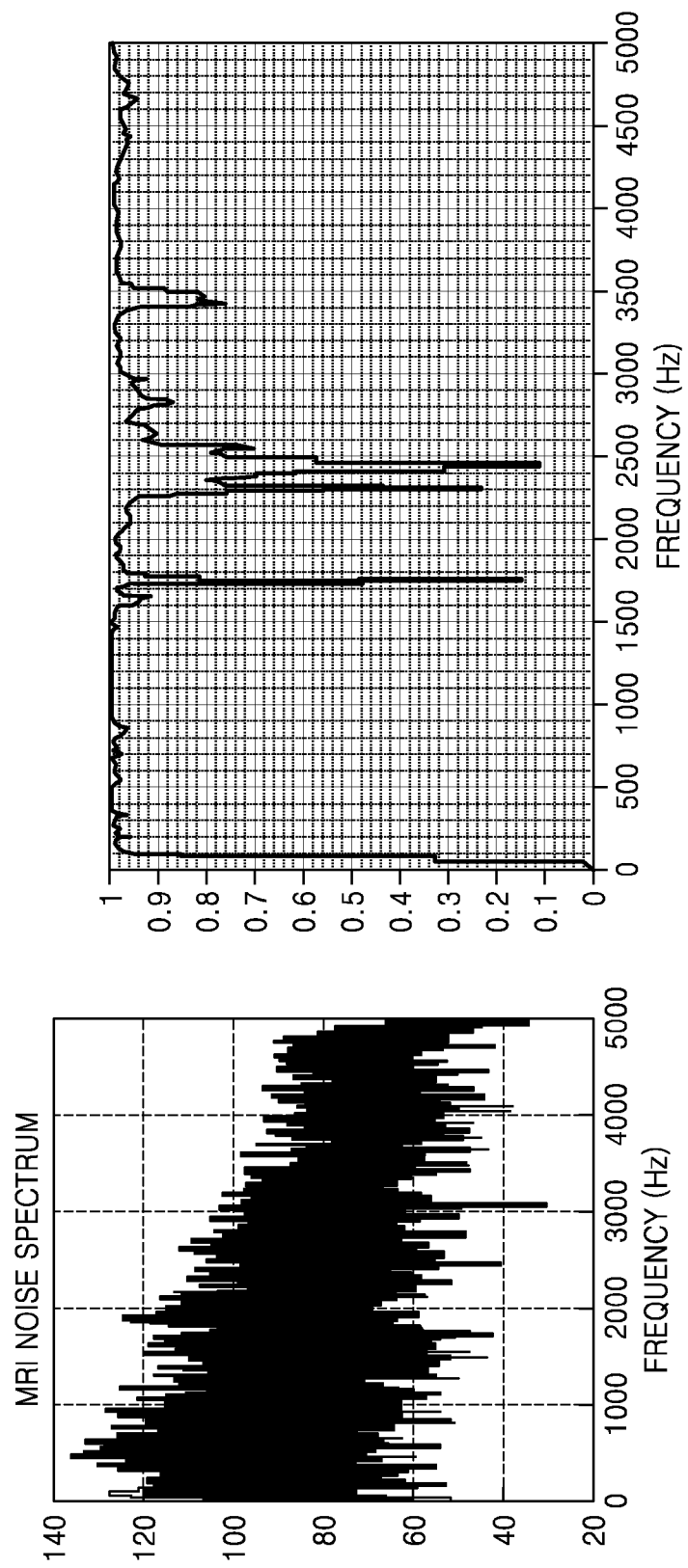
FIG. 4 illustrates frequency characteristics of an MRI noise signal and coherence between a speaker and an acquisition unit according to an embodiment.

240. Otherwise, if the output interface 240 and the acquisition unit 360 have low coherence therebetween, this means that the acquisition unit 360 may unsuccessfully acquire a signal output from the output interface 240. For example, coherence between the output interface 240 and the acquisition unit 360 may be increased or decreased according to the performance of the output interface 240 and the acquisition unit 360 with respect to each frequency or effects of space. According to an embodiment, the target frequency determiner 330 may exclude a frequency where coherence between the output interface 240 and the acquisition unit 360 is less than or equal to 0.7 from candidates for target frequencies. FIG. 4 illustrates frequency characteristics of the MRI noise signal 210 and coherence between the output interface 240 and the acquisition unit 360 according to an embodiment.

The reference signal generator 340 may generate a reference signal corresponding to a specific target frequency. The reference signal means a signal that becomes the basis for generating the control signal 245 for each target frequency. After the control signal 245 is output from the output interface 240, the control signal 245 reaches a position of the acquisition unit 360 through a transfer function and cancels out the MRI noise signal 210 to reduce MRI noise. As described below, the control signal 245 may be generated for each target frequency by applying an amplitude and a phase determined by the filter determiner 370 to a reference signal generated for each target frequency.

According to an embodiment, the reference signal generator 340 may generate a reference signal by acquiring the MRI noise signal 210 before the MRI noise signal 210 reaches a desired position (i.e., a position of the acquisition unit 360) where noise is to be controlled by placing a reference microphone (not shown) close to a noise source. According to an embodiment, the reference signal generator 340 may generate a reference signal by using the MRI noise signal 210 that has been previously acquired via the acquisition unit 360 instead of using the reference microphone.

A reference signal generated for each target frequency may include a cosine wave and a sine wave that have a specific target frequency as a fundamental frequency. According to an embodiment, the reference signal generator 340 may generate a first reference signal (a cosine wave) and a second reference signal (a sine wave) for an MRI noise signal $A*\cos(w_0*n)$ corresponding to a specific target frequency $w_0$. When an amplitude and a phase of the MRI noise signal $A*\cos(w_0*n)$ corresponding to the specific target frequency $w_0$ change, a control signal $A'*\cos(w_0*n+\theta)$ corresponding to the target frequency $w_0$ is generated. As shown in Equation (4), the control signal $A'*\cos(w_0*n+\theta)$ corresponding to the target frequency $w_0$ may be represented as a combination of $\cos(w_0*n)$ and $\sin(w_0*n)$:

$$A'*\cos(w_0*n+\theta)=A'*\cos(\theta)\cos(w_0*n)-A'\sin(\theta)\sin(w_0*n) \quad \text{[Equation (4)]}$$

In detail, the reference signal generator 340 may determine a first reference signal $\cos(w_0*n)$ and a second reference signal $\sin(w_0*n)$ corresponding to the target frequency $w_0$. $A'\cos(\theta)$ and $A'*\sin(\theta)$ respectively represent filter values for the first and second reference signals, which are determined by the filter determiner 350 as described below.

According to an embodiment, the reference signal generator 340 may calculate first and second reference signals corresponding to a specific target frequency and store the first and second reference signals in a table before the MRI system 100 starts to operate and read a reference signal from the table. According to an embodiment, the reference signal generator 340 may generate a reference signal in real time by using Equation (5):

$$w_0=\text{target frequency}/fs \text{ (sampling frequency)}$$

$$\text{first reference signal } (n)=q1-\cos(w_0)*q0$$

$$\text{second reference signal } (n)=\sin(w_0)*q0$$

$$q0=q1$$

$$q1=2*\cos(w_0)*q1-q0 \quad \text{[Equation (5)]}$$

The filter determiner 350 may determine a filter that is to be applied to a reference signal generated by the reference signal generator 340. The filter determiner 350 may calculate an amplitude and a phase of the MRI noise signal 210 acquired via the acquisition unit 360. The filter determiner 350 may perform a Fourier series expansion on the MRI noise signal 210 acquired via the acquisition unit 360 for each of the target frequencies determined by the target frequency determiner 330 and calculate an amplitude and a phase of the MRI noise signal corresponding to each target frequency.

According to an embodiment, the filter determiner 350 may calculate an amplitude A' and a phase $\theta$ for each target frequency of the MRI noise signal 210 that has been acquired via the acquisition unit 360 during a specific time period T2 and respectively determine $A'*\cos(\theta)$ and $A'*\sin(\theta)$ as being filter values for first and second reference signals. A filter value includes an amplitude and a phase for each target frequency.

Figure 5:
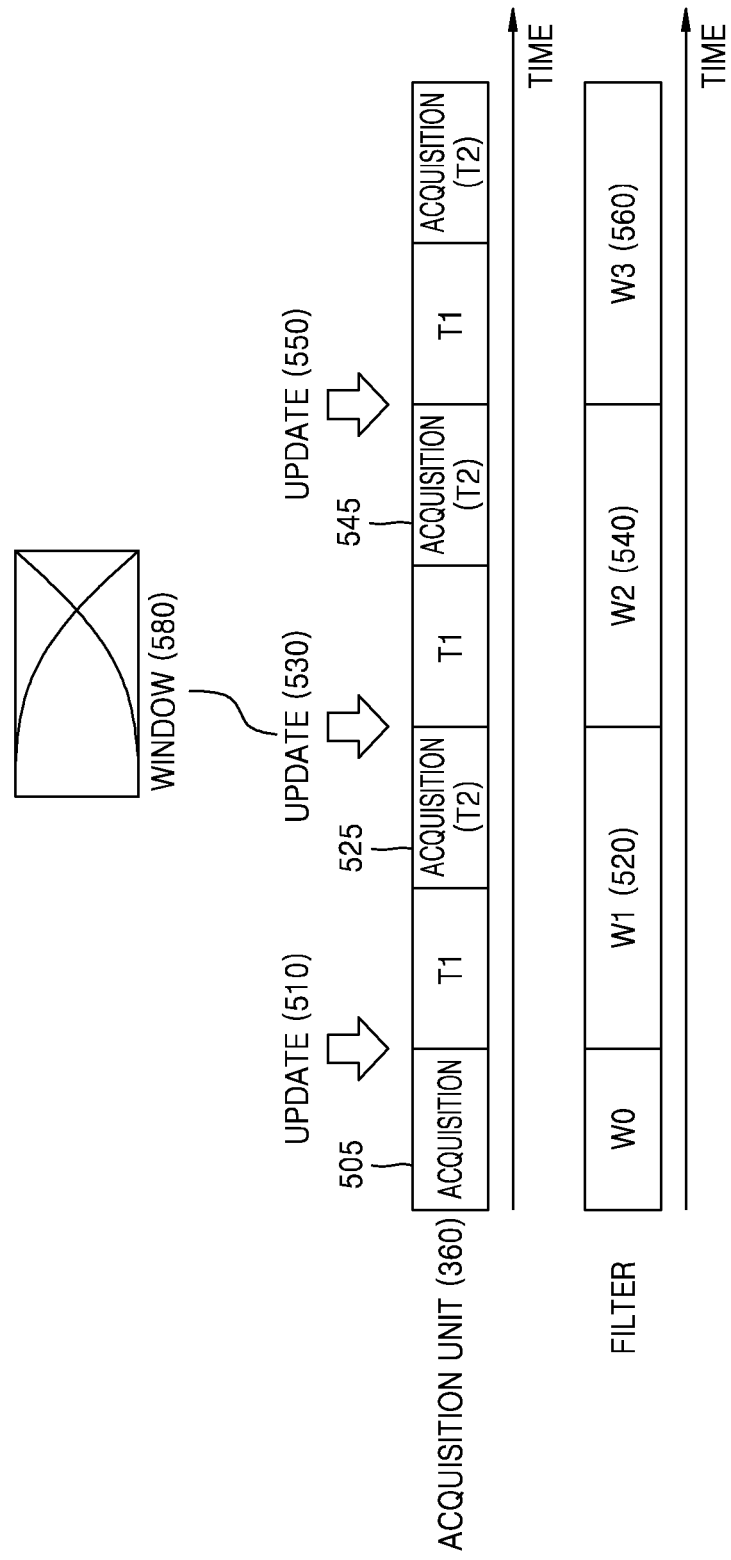
FIG. 5 illustrates an update of a filter for generating a control signal at each target frequency over time, according to an embodiment.

Referring to FIG. 5, the filter determiner 350 may acquire data with respect to the MRI noise signal 210 during a time period T2 after a time period T1 elapsed from the time when a filter updated. The time period T1 may be determined by a transit time required to stabilize a response of the output interface 240.

After determining an amplitude and a phase for each target frequency, the filter determiner 350 may update a filter. Referring to FIG. 5, the filter determiner 350 may calculate an amplitude and a phase based on a signal acquired (505) via the acquisition unit 360 and update an existing filter with a filter W1 520 (510). Furthermore, the filter determiner 350 may calculate an amplitude and a phase based on a signal acquired (525) via the acquisition unit 360 and update an existing filter with a filter W2 540 (530). In addition, the filter determiner 350 may calculate an amplitude and a phase based on a signal acquired (545) via the acquisition unit 360 and update an existing filter with a filter W3 560 (550). In detail, the filter determiner 350 may determine a filter value for generating a current control signal 245 based on a MRI noise signal 210 that was previously acquired at a desired position where the MRI noise signal 210 is to be controlled, and generate the control signal 245 by applying the determined filter value to a reference signal.

When a filter value (an amplitude and a phase) undergoes an abrupt and large change during an update, distortion may occur. Thus, the filter determiner 370 may apply a window 580 between filter values from previous and current frames.

The filter applying unit 360 may apply a filter determined with respect to each target frequency to a reference signal generated for each target frequency to thereby generate a control signal for each target frequency. As described above, the control signal corresponding to a target frequency $w_0$ is a signal obtained by changing at least one of an amplitude and a phase of the MRI noise signal at the target frequency $w_0$.

The filter applying unit 360 may generate a control signal $A'^*\cos(w_0^*n+8)$ for an MRI noise signal $A^*\cos(w_0^*n)$ corresponding to the target frequency by using a first reference signal $\cos(w_0^*n)$, a second reference signal $\sin(w_0^*n)$, and filter values $A'^*\cos(\theta)$ and $A'^*\sin(\theta)$ based on Equation (4). The filter applying unit 360 may generate control signals respectively corresponding to target frequencies, and transmit the generated control signals to the output interface 240 by summing the generated control signals.

The output interface 240 may output the sum of control signals 245 respectively generated for target frequencies to thereby control the corresponding MRI noise signals 210 at a position of the acquisition unit 360 and reduce MRI noise.

Figure 6:
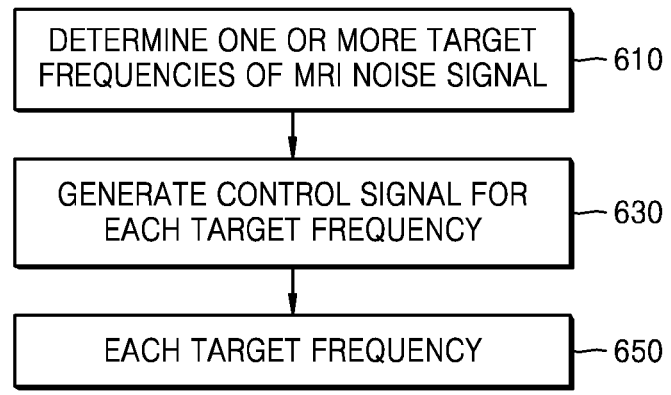
FIG. 6 is a flowchart of a method according to an embodiment.

FIG. 6 is a flowchart of a method according to an embodiment.

Since FIG. 6 is a flowchart of a method, performed by the apparatus 200 or 300 described with reference to FIGS. 2 through 5, of controlling MRI noise, the descriptions above of the apparatus 200 or 300 with respect to FIG. 6 apply to the method though omitted hereinafter.

The apparatus 200 may determine one or more target frequencies of the MRI noise signal 210 generated within the MRI system 100 (step 610). A target frequency means a desired frequency of the MRI noise signal 210 to be controlled.

The apparatus 200 may determine MRI sequence period information based on information about an MRI sequence used to drive a gradient coil of the MRI system 100 and determine a period of the MRI noise signal 210 based on the MRI sequence period information. Alternatively, instead of acquiring the period information from the information about MRI sequence, the apparatus 200 may determine the period of the MRI noise signal 210 by acquiring the MRI noise signal 210 via the acquisition unit 360 and analyzing the acquired MRI noise signal 210. The apparatus 200 may determine a fundamental frequency of the MRI noise signal 210 based on the determined period information. The apparatus 200 may determine one or more harmonic frequencies composing the MRI noise signal 210 by using the determined fundamental frequency. In other words, the apparatus 200 may select one or more harmonic frequencies among harmonic frequencies that are multiples of the fundamental frequency in order to determine the target frequencies. The apparatus 200 may select a predetermined number of harmonic frequencies from among the one or more harmonic frequencies, based on at least one of energy information at each frequency and coherence between a speaker and the acquisition unit 360, and determine the selected harmonic frequencies as the target frequencies.

The apparatus 200 may generate the control signal 245 for each of the determined one or more target frequencies (step 630). The control signal 245 generated for each target frequency is a signal obtained by changing at least one of an amplitude and a phase of the MRI noise signal 210. The control signal 245 reaches a desired position where the MRI noise signal 210 is to be controlled through a transfer function to cancel out the MRI noise signal 210.

Before generating the control signal 245, the apparatus 200 may generate a reference signal that is the basis of the control signal 245 for each target frequency. The reference signal becomes the basis for generating the control signal 245 and may be generated by acquiring the MRI noise signal 210 before the MRI noise signal 210 reaches a desired position where noise is to be controlled or by using the previously acquired MRI noise signal 210. The apparatus 200 may generate a control signal for each target frequency by applying a filter value to a reference signal. A reference signal corresponding to a specific target frequency may include a cosine wave and a sine wave that have the specific target frequency as a fundamental frequency.

The apparatus 200 may output the generated control signal 245 (step 650). The apparatus 200 may add together the control signals 245 respectively generated for the target frequencies and output the sum of control signals 245. The output control signal 245 may reach a desired position where noise is to be controlled through a transfer function and cancel out and control the MRI noise signal 210.

Figure 7:
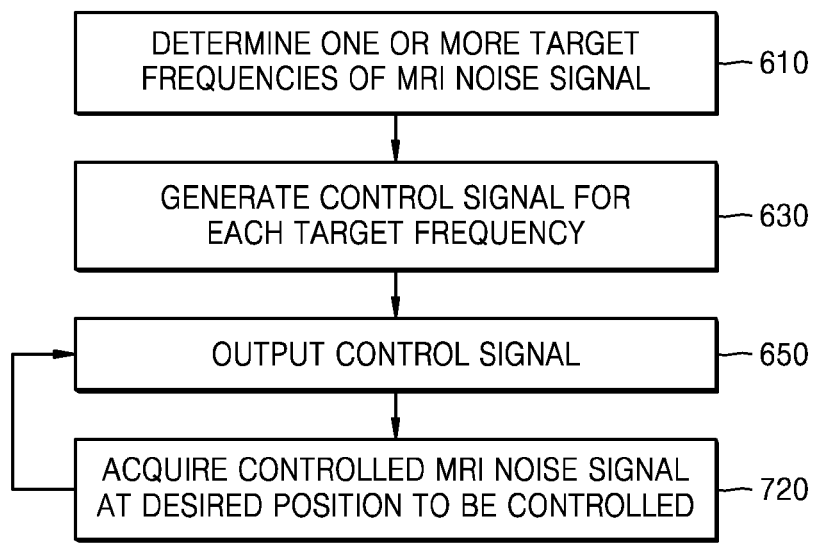
FIG. 7 is a flowchart of a method according to another embodiment.

FIG. 7 is a flowchart of a method according to another embodiment.

The descriptions of steps 610, 620, and 650 already provided with respect to FIG. 6 will be omitted below.

The apparatus 200 may acquire the MRI noise signal 210 at a desired position where the MRI noise signal 210 is to be controlled (step 720). In other words, the MRI noise signal 210 acquired in step 720 may be a noise signal obtained after the original MRI noise signal 210 is controlled by the control signal 245. The apparatus 200 may acquire the MRI noise signal 210 corresponding to each target frequency at a desired position where the MRI noise signal 210 is to be controlled during a predetermined time period and perform a Fourier series expansion on the acquired MRI noise signal 210 to thereby determine a filter value including an amplitude and a phase of the MRI noise signal 210. The method returns to step 630 in order to transmit the determined filter value. The apparatus 200 applies the filter value to a reference signal generated for each target frequency to generate a control signal for each target frequency. In detail, the apparatus 200 may determine a filter value for generating a current control signal 245 based on a previous MRI noise signal 210 that was acquired at a desired position where the MRI noise signal 210 is to be controlled and generate the control signal 245 by applying the determined filter value to the reference signal.

The above-described methods according to the embodiments may be embodied as computer-readable code on a computer-readable storage medium. The computer-readable storage medium is any data storage device that can store data which can be thereafter read by a computer system. Examples of computer-readable storage media include read-only memory (ROM), random-access memory (RAM), CD-ROMs, magnetic tapes, floppy disks, optical data storage devices, carrier waves such as transmission through the Internet, etc. Furthermore, the computer-readable storage media can also be distributed over network-coupled computer systems so that processor-readable code is stored and executed in a distributed fashion.

The methods, processes, apparatuses, products, and/or systems according to the present invention are straightforward, cost-effective, uncomplicated, highly versatile, and accurate. Furthermore, the processes, apparatuses, products, and the systems of the invention can be implemented by applying known components thereto for ready, efficient, and economical manufacturing, applications, and utilization. Another important aspect of the present invention is that it meets the current trends toward cost reduction, system simplification, and enhanced performance. Useful features of embodiments of the invention may consequently improve current technology to at least the next level.

While the invention has been described with reference to a specific best mode, it should be understood that substitutions, modifications, and changes made therein will be apparent to those skilled in the art in view of the foregoing description. In other words, the scope of the appended claims should be construed as including all the substitutions, modifications, and changes. Thus, the above embodiments and all aspects thereof set forth herein or shown in the accompanying drawings should be interpreted in an illustrative and non-limiting sense.

The invention claimed is:

1. An apparatus comprising:
a controller configured to determine a fundamental frequency of a magnetic resonance imaging (MRI) noise signal generated in an MRI system, determine harmonic frequencies of the determined fundamental frequency, determine target frequencies among the harmonic frequencies, generate a reference signal for each of the target frequencies, and generate a control signal by summing reference, signals generated for each of the target frequencies; and
an output interface configured to output the control signal,
wherein the target frequency is a desired frequency of the MRI noise signal to be controlled, and
wherein the controller is further configured to determine an amplitude and a phase for each of the target frequencies, and generate the control signal by applying the determined amplitude and phase of reference signal generated for each of the target frequencies.

2. The apparatus of claim 1, further comprising an acquisition unit configured to acquire the MRI noise signal at a desired position where the MRI noise signal is to be controlled.

3. The apparatus of claim 2, wherein the target frequencies are a predetermined number of harmonic frequencies that are selected from among the determined harmonic frequencies based on energy information with respect to each frequency.

4. The apparatus of claim 2, wherein the target frequencies are a predetermined number of harmonic frequencies that are selected from among the determined harmonic frequencies based on coherence between the output interface and the acquisition unit.

5. The apparatus of claim 2, wherein the controller is further configured to determine a period of the MRI noise signal based on information about an MRI sequence used to drive a gradient coil in the MRI system, and the fundamental frequency is determined based on the determined period.

6. The apparatus of claim 2, wherein the controller is further configured to determine a period of the MRI noise signal by analyzing the MRI noise signal acquired by the acquisition unit, and the fundamental frequency is determined based on the determined period.

7. The apparatus of claim 2, wherein a control signal reaches a position of the acquisition unit to cancel out the MRI noise signal.

8. The apparatus of claim 7, wherein the reference signal generated for each of the target frequencies comprises a cosine wave and a sine wave that have a target frequency as a fundamental frequency.

9. The apparatus of claim 7, wherein the controller is further configured to perform a Fourier series expansion on the MRI noise signal, which has been acquired by the acquisition unit during a predetermined time period, for each of the target frequencies to thereby determine the amplitude and the phase for each of the target frequencies.

10. The apparatus of claim 1, wherein the fundamental frequency is determined based on information about a TR and a number of slices in an MRI sequence used to drive a gradient coil in the MRI system.

11. The apparatus of claim 2, wherein the fundamental frequency is determined based on a maximum autocorrelation value among autocorrelation values for the MRI noise signal acquired by the acquisition unit.

12. A method comprising:
determining a fundamental frequency of a magnetic resonance imaging (MRI) noise signal generated in an MRI system;
determining harmonic frequencies of the determined fundamental frequency;
determining target frequencies among the harmonic frequencies;
generating a control signal by summing reference signals generated for each of the target frequencies; and
outputting the generated control signal,
wherein the target frequency is a desired frequency of the MRI noise signal to be controlled, and
wherein the generating of the control signal comprises determining an amplitude and a phase for each of the target frequencies, and generating the control signal by applying the determined amplitude and phase to the reference signal generated for each of the target frequencies.

13. The method of claim 12, further comprising acquiring the MRI noise signal at a desired position where the MRI noise signal is to be controlled.

14. The method of claim 13, wherein the control signal reaches a position of an acquisition unit to cancel out the MRI noise signal, and
wherein the determining of the amplitude and the phase comprises:
performing a Fourier series expansion on the MRI noise signal, which has been acquired during a predetermined time period, for each of the target frequencies to thereby determine the amplitude and the phase for each of the target frequencies.

15. A non-transitory computer-readable recording medium having recorded thereon a program for executing the method of claim 12 on a computer.

16. A non-transitory computer-readable recording medium having recorded thereon a program for executing the method of claim 13 on a computer.

17. A non-transitory computer-readable recording medium having recorded thereon a program for executing the method of claim 14 on a computer.

* * * * *